(12) United States Patent
Pfeiffer

(10) Patent No.: US 6,485,305 B1
(45) Date of Patent: *__Nov. 26, 2002__

(54) BLANK FOR PRODUCING A FORMED DENTAL PART

(75) Inventor: Joachim Pfeiffer, Bensheim (DE)

(73) Assignee: Sirona Dental Systems GmbH, Bensheim (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 426 days.

(21) Appl. No.: 08/824,500

(22) Filed: Mar. 27, 1997

(30) Foreign Application Priority Data

Mar. 29, 1996 (DE) .......................... 196 12 699

(51) Int. Cl.[7] ................................. A61C 13/08
(52) U.S. Cl. ...................... 433/202.1; 433/49; 433/223; 428/542.8
(58) Field of Search ................................. 433/223, 218, 433/219, 213, 202.1, 49; 29/896.1; 428/542.8

(56) References Cited

U.S. PATENT DOCUMENTS

| 4,457,714 A | * | 7/1984 | Klein .......................... 433/213 |
| 4,615,678 A | | 10/1986 | Moermann et al. ...... 433/201.1 |
| 4,684,555 A | * | 8/1987 | Neumeyer ................ 433/202.1 |
| 5,151,044 A | * | 9/1992 | Rotsaert .................. 433/202.1 |
| 5,342,696 A | * | 8/1994 | Eidenbenz et al. ........... 433/49 |

FOREIGN PATENT DOCUMENTS

| DE | 40 30 176 | 3/1992 |
| DE | 40 30 185 | 3/1992 |
| EP | 0 160 797 | 1/1989 |
| EP | 0 455 853 | 11/1991 |

* cited by examiner

*Primary Examiner*—John J. Wilson
(74) *Attorney, Agent, or Firm*—Schiff Hardin & Waite

(57) ABSTRACT

A blank for producing a formed dental part has closely toleranced reference faces being arranged at one end of a blank member lying opposite a retainer projection. The reference faces comprise two surfaces lying opposite one another that have a defined spacing from one another with close tolerances. The surfaces are advantageously formed by a reference part with a cylindrical cross section that is secured onto the blank member.

7 Claims, 1 Drawing Sheet

BLANK FOR PRODUCING A FORMED DENTAL PART

BACKGROUND OF THE INVENTION

The present invention is directed to a blank for producing a formed dental part, which blank comprises a blank member of a tooth restoration material from which the formed part can be produced with a tool, a retaining projection for holding the blank member in the processing machine and a reference face having close tolerances for engagement by the tool for the purpose of calibration of the tool.

U.S. Pat. No. 4,615,678, whose disclosure is incorporated herein by reference thereto and which claims priority from the same Swiss Application as European Patent 0 160 797, discloses a blank, which can be machined or formed into a dental part. The blank is composed of the blank member of the tooth restoration material from which the actual dental part, such as an in lay, on lay, bridge or the like, can be produced and, in addition, has a retainer projection connected to the blank member. The purpose of the retainer projection is always to clamp the blank in an unambiguous position in the processing means or machine on the basis of a stop face and to be able to simultaneously exactly center the blank. To this end, the retainer projection contains at least one stop face for defining the angular position and, at its end face toward the blank member, a reference face that is arranged concentrically relative to the cylindrical axis and is exposed for the grinding tool and is cylindrical at least in sections. Within a narrow tolerance, the reference face has a predetermined, radial spacing from the axis of the retainer projection and serves the purpose of being able to define the position and critical dimensions of the processing tool, for example, the diameter of a grinding disk. This calibration, i.e., the definition of the reference point of the tool, occurs in that the tool is brought toward or, respectively, touches the calibration location with a small tolerance reference face before the beginning of the process.

In the known blank, the retainer projection must be very precisely fabricated in order to be able to adhere to the required position of ±0.01 mm. In terms of fabrication, thus, the retainer projection is of a high-quality part, so that simple manufacturing methods, such as, for example, injection molding, impact molding, die-casting, metal sintering or the like, therefore, do not come into consideration for the manufacture of the retainer.

SUMMARY OF THE INVENTION

The present invention is directed to an object of providing a blank wherein the retaining projection can be more economically produced, but the procession of the required reference or, respectively, touching faces can be enhanced given minimization of the manufacturing cost.

To obtain this object, the present invention is directed to a blank for producing a formed part that can be used for replacement or restoration of one or more teeth by removing material with at least one tool chucked in a processing machine, with the blank consisting of a blank member of the tooth restoration material from which the formed part can be worked with the tool, a retainer projection for holding the blank member in the processing machine being positioned at one end of the blank member, and a reference face being arranged at an end of the blank member opposite the retainer projection and containing at least two face elements or surfaces having a defined spacing from one another with a close tolerance.

In that the functions of retaining, on the one hand, and the touching of the reference faces, on the other hand, are separated from one another in the inventively manufactured blank, the retainer projection itself can be very cost-beneficially produced. That part on the end of the blank member lying opposite the retainer projection and containing the reference faces or surfaces, however, can also be comparatively cost-beneficially manufactured. The reference part can, thus, be advantageously cut to length from a rod material. Alternatively, a precision-fit pin or a roller bearing can be employed. The part can be put in place on the blank member without an exact positioning relative to the cylindrical axis of the retainer projection being necessary. As the simplest solution, it is proposed to provide a circular-cylindrical set part. However, it is conceivable and also lies within the framework of the invention to employ a cuboid or similarly-fashioned part. More than two surfaces can thus be potentially required for the calibration, given a lower symmetry of the set part.

The invention is based on the perception that the rotational axis of the processing machine is the only important reference quantity for the tool position and size. Differing from previous practice, the retainer projection need not be utilized for defining the size and position definition of the tool, which usually occurs by approaching or touching at least two reference faces having close tolerances, and this retainer projection need not be manufactured in a relatively complicated manner. On the contrary, a set part independent of the retainer projection suffices, and only this part needs to be constructed with close tolerances. This set part can then be secured to the blank member of the material without adhering to greater dimensional accuracy. Even though the set part need only comprise two reference faces lying opposite one another in the simplest case, with these faces or surfaces having a defined spacing from one another, it is expedient and advantageous to provide a cylindrical set part having a circular cross section. The position and critical dimensions of the processing tool, for example the exact current diameter of the grinding disk or, respectively, the spacing of the grinding disk or an end-milling cutter from the rotational axis of the processing machine, can thus be easily mathematically determined given the known spacing that the two reference surfaces have from one another.

Other advantages and features of the invention will be readily apparent from the following description of the preferred embodiments, the drawings and claims.

DESCRIPTION OF THE PREFERRED EMBODIMENTS

Figure 1:
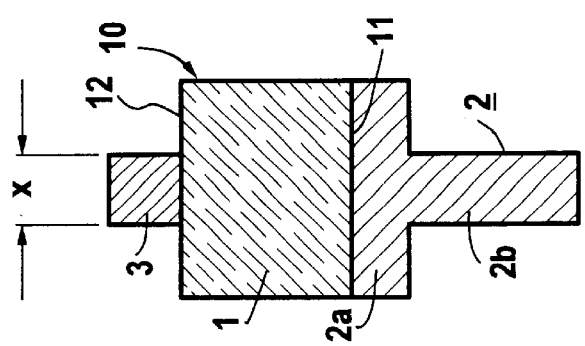
FIG. 1 is a longitudinal cross sectional view taken along the axis of a blank in accordance with the present invention.

The principles of the present invention are particularly useful when incorporated in the inventive blank, which is generally indicated at 10 in FIG. 1. The blank 10 includes a blank member or body 1 composed of a material standard in dental technology, for example ceramic material, and from which the formed part is to be fabricated later by removal of the material. The blank member 1 has a cylindrical form, which preferably has a circular-cylindrical cross section. The body 1 has relatively rough dimensions, as far as tolerance, and, as a result, the manufacturing process, such as pressing, casting, sintering or the like, is not made difficult. Typically, the tolerances lie in a range of ±$^2$/$_{10}$ mm.

In a known way, a retainer projection 2 adjoins an end face 11 of the blank member or body 1. The retainer projection 2 comprises a circular-cylindrical flange 2a with a thickness that is adequate in order to enable a reliable securing to the body 1, for example by gluing. An acceptance shaft 2b of the retainer projection 2 is dimensioned so that it fits into a predetermined receptacle or chuck of a processing machine. The tolerance of the diameters 2a and 2b can be selected so that a cost-beneficial manufacture is possible. Typically, this likewise lies in a range of ±$^2$/$_{10}$ mm. The connecting of the parts 1 and 2 is not subject to any specific demands in terms of adhering to centricity or, respectively, concentricity. The concentricity can lie in the range of the afore-mentioned rough tolerances of ±$^2$/$_{10}$ mm. Accordingly, the retainer projection 2 can be manufactured according to a varied cost-beneficial method, such as the initially-mentioned injection molding.

A set part 3 is placed on an end face 12 of the blank member 1 lying opposite the retainer projection 2 and the end face 11. The set part 3 serves the purpose of defining the size and position of the processing tool, and, by contrast to the retainer projection 2, has close tolerances, for example, it has fabrication dimensions typically lie in the range of tolerances of ±$^1$/$_{100}$ mm. A circular cylinder fabricated of metal is preferably utilized for the part 3, wherein the cylindrical diameter is inherently arbitrarily selected. A set member 3 is placed centrally on the blank member 1 of the material, whereby, however, there are no specific demands made of the concentricity relative to the parts 1 and 2. The only thing that is critical is that a parallelism of the cylinder faces is established, at least at two locations turned 180°, and the spacing x between these surfaces from one another is known. The connection between the parts 1 and 3 can occur by gluing.

The set part 3 can also be utilized for type identification on the basis of a predetermined combination of a graduation.

Figure 2:
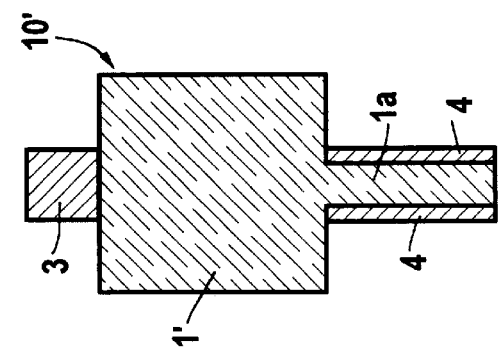
FIG. 2 is a longitudinal cross sectional view of an embodiment of the blank of FIG. 1.

FIG. 2 shows a modification or embodiment of a blank 10' with a blank member 1' comprising a peg-shaped continuation 1a that is provided with a coating 4 of tenacious material, such as plastic or metal. The coating serves the purpose of avoiding breakage when securing the blank in a corresponding holding mechanism of the processing machine. The dimensional demands made of the retainer projection 1a and the coating or sleeve 4 also lie in a range of ±$^2$/$_{10}$ mm. The retainer projection need not have close tolerances.

Figure 3:
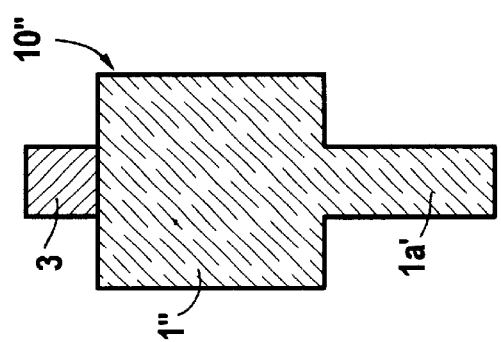
FIG. 3 is a longitudinal cross sectional view of a second embodiment of the blank of FIG. 1.

FIG. 3 shows a second embodiment of a blank 10" with a blank member 1" that has the retainer projection 1a', which is immediately matched to the required dimensions of the receptacle means of the processing machine. Such a construction is appropriate when the corresponding retaining mechanism is constructed such that it is suitable for the acceptance of the retainer projection composed of tooth replacement material.

Figure 4:
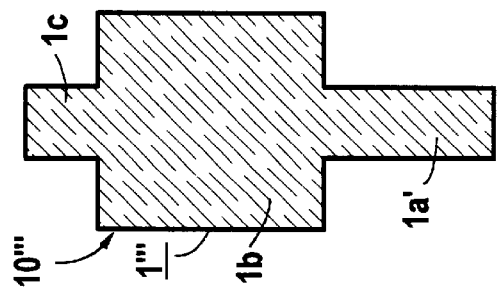
FIG. 4 is a longitudinal cross sectional view of a third embodiment of a blank in accordance with FIG. 1.

A fourth embodiment is illustrated in FIG. 4 and comprises a blank 10''' which has a member 1''' having a retainer projection 1a' extending from the body portion 1b. A set part 1c is fabricated as an integral part of the body portion 1b. Such a modification is especially appropriate when it is technologically possible to more easily adhere to a close tolerance, as required for the set part 3, given the material employed, respectively, to more easily process the material with close tolerances.

As already initially addressed, various modifications are possible, in view of the shaping of the contour of the set part 3. In addition to the cylindrical set parts described in the exemplary embodiments, which have the advantage that they can be practically cut to length from a rod of material that comprises the above-mentioned, close tolerances or that, typically, only two surfaces are required at two angles relative to the workpiece axis, it is likewise possible to provide cuboid set parts for differently constructed set parts. As has already been pointed out, there is the sole condition that at least two reference faces, which lie opposite one another, must be present. These reference faces have close tolerances and have an exact, defined spacing from one another.

Although various minor modifications may be suggested by those versed in the art, it should be understood that I wish to embody within the scope of the patent granted hereon all such modifications as reasonably and properly come within the scope of my contribution to the art.

I claim:

1. A blank for producing a formed part that can be used for replacement or restoration of one or more teeth by removing material with at least one tool chucked in a processing machine, said blank comprising a blank member of a tooth restoration material from which the formed part can be worked with a tool, a retainer projection extending from one end of the blank member for holding the blank member in the processing machine, and a separate reference part having a circular-cylindrical cross section and containing at least two reference surfaces that are defined with a space between one another with a close tolerance in a range of ±$^1$/$_{100}$ mm, said reference part being secured in place on an end of the blank member lying opposite the retainer projection, the diameter of the retainer projection, the concentricity of the blank member and the concentricity of the reference surface in respect to the retainer projection having tolerances in a range of ±$^2$/$_{10}$ mm, which are rough tolerances compared with the close tolerances of the two reference surfaces of the reference part.

2. A blank for producing a formed part that can be used for replacement or restoration of one or more teeth by removing material with at least one tool chucked in a processing machine, said blank comprising a blank member of a tooth restoration material from which the formed part can be worked with a tool, a retainer projection extending from one end of the blank member for holding the blank member in the processing machine, and a reference part being a member having a circular-cylindrical cross section and formed of a rod material cut to length, said reference part being arranged at an end of the blank member lying opposite the retainer projection, said reference part having at least two reference surfaces that are defined with a space between one another with close tolerances in a range of ±$^1$/$_{100}$ mm, the diameter of the retainer projection, the concentricity of the blank member and the concentricity of the reference surface in respect to the retainer projection having tolerances in a range of ±$^2$/$_{10}$ mm, which are rough tolerances compared with the close tolerances of the two reference surfaces of the reference part.

3. A blank for producing a formed part that can be used for replacement or restoration of one or more teeth by removing material with at least one tool chucked in a processing machine, said blank comprising a blank member of a tooth restoration material from which the formed part can be worked with a tool, a retainer projection extending from one end of the blank member for holding the blank member in the processing machine, and a reference part being arranged at an end of the blank member lying opposite the retainer projection, the reference part being formed of a set pin, having a circular-cylindrical cross section, said reference part having at least two reference surfaces that are defined with a space between one another with close tolerances in a range of ±1/100 mm, the diameter of the retainer projection, the concentricity of the blank member and the concentricity of the reference surface in respect to the retainer projection having tolerances in a range of ±2 mm, which are rough tolerances compared with the close tolerances of the two reference surfaces of the reference part.

4. A blank for producing a formed part that can be used for replacement or restoration of one or more teeth by removing material with at least one tool chucked in a processing machine, said blank comprising a blank member of a tooth restoration material from which the formed part can be worked with a tool, a retainer projection extending from one end of the blank member for holding the blank member in the processing machine, and a reference part being formed of a cylindrical roller, said reference part being arranged at an end of the blank member lying opposite the retainer projection, said reference part having at least two reference surfaces that are defined with a space between one another with close tolerances in a range of ±1/100 mm, the diameter of the retainer projection, the concentricity of the blank member and the concentricity of the reference surface in respect to the retainer projection having tolerances in a range of ±2/10 mm, which are rough tolerances compared with the close tolerances of the two reference surfaces of the reference part.

5. A blank for producing a formed part that can be used for replacement or restoration of one or more teeth by removing material with at least one tool chucked in a processing machine, said blank comprising a blank member of a tooth restoration material from which the formed part can be worked with a tool, a retainer projection extending from one end of the blank member for holding the blank member in the processing machine, the retainer projection and the blank member being composed of the same material and a reference part being glued onto an end of the blank member lying opposite the retainer projection, said reference part having at least two reference surfaces that are defined with a space between one another with close tolerances in a range of ±1/100 mm, the diameter of the retainer projection, the concentricity of the blank member and the concentricity of the reference surface in respect to the retainer projection having tolerances in a range of ±2/10 mm, which are rough tolerances compared with the close tolerances of the two reference surfaces of the reference part.

6. A blank for producing a formed part that can be used for replacement or restoration of one or more teeth by removing material with at least one tool chucked in a processing machine, said blank comprising a blank member of a tooth restoration material from which the formed part can be worked with the tool, a retainer projection extending from one end of the blank member for holding the blank member in the processing machine, the retainer projection comprising a sleeve mounted on a projection of a blank member and a reference part being a separate member attached to an end of the blank member lying opposite the retainer projection, said reference part having at least two reference surfaces that are defined with a space between one another with close tolerances, the diameter of thee retainer projection, the concentricity of the blank member and the concentricity of the reference surfaces in respect to the retainer projection having rough tolerances compared to the two reference surfaces with close tolerance.

7. A blank according to claim 6, wherein the close tolerances are ±1/100 mm and the rough tolerances are ±2/10 mm.

* * * * *